(12) United States Patent
Rispoli et al.

(10) Patent No.: US 9,085,759 B2
(45) Date of Patent: Jul. 21, 2015

(54) PROCESS FOR THE PRODUCTION OF ALGAL BIOMASS WITH A HIGH LIPID CONTENT

(75) Inventors: Giacomo Rispoli, Rome (IT); Emiliano Fioravanti, Rome (IT); Renzo Bignazzi, Legnano (IT); Ezio Nicola D'Addario, Monterotondo (IT); Francesca De Ferra, Lodi (IT); Federico Capuano, Rieti (IT)

(73) Assignee: ENI S.p.A., Rome (IT)

( * ) Notice: Subject to any disclaimer, the term of this patent is extended or adjusted under 35 U.S.C. 154(b) by 219 days.

(21) Appl. No.: 12/747,990

(22) PCT Filed: Dec. 3, 2008

(86) PCT No.: PCT/EP2008/010291
§ 371 (c)(1),
(2), (4) Date: Sep. 20, 2010

(87) PCT Pub. No.: WO2009/077087
PCT Pub. Date: Jun. 25, 2009

(65) Prior Publication Data
US 2011/0020913 A1    Jan. 27, 2011

(30) Foreign Application Priority Data

Dec. 14, 2007    (IT) .............................. MI2007A2343

(51) Int. Cl.
*C12N 1/12*    (2006.01)
*C12M 1/00*    (2006.01)

(52) U.S. Cl.
CPC ................. *C12N 1/12* (2013.01); *C12M 21/02* (2013.01); *C12M 23/18* (2013.01); *C12M 29/02* (2013.01); *C12M 43/04* (2013.01); *C12M 47/02* (2013.01); *C12M 47/06* (2013.01)

(58) Field of Classification Search
CPC ........................................................ C12N 1/12
USPC ..................................................... 435/257.1
See application file for complete search history.

(56) References Cited

U.S. PATENT DOCUMENTS

| | | | |
|---|---|---|---|
| 4,236,349 A | 12/1980 | Ramus | |
| 2006/0286648 A1 | 12/2006 | Bailey et al. | |
| 2006/0286649 A1 | 12/2006 | Bailey et al. | |
| 2008/0096267 A1* | 4/2008 | Howard et al. ............ | 435/257.1 |
| 2008/0299643 A1 | 12/2008 | Howard et al. | |

FOREIGN PATENT DOCUMENTS

| WO | 94 07993 | 4/1994 |
|---|---|---|
| WO | 01 54510 | 8/2001 |
| WO | 01 74990 | 10/2001 |
| WO | 2007 025145 | 3/2007 |
| WO | 2007 109066 | 9/2007 |

OTHER PUBLICATIONS

Moheimani et al. (The Long-term culture of the cocclithophore *Pleurochrysis carterae* (Haptophyta) in outdoor raceway pond. Journal of Applied Phycology (2006) 18: 703-712.*
Olaizola et al. (Commercial production of astaxanthin from *Haemotococcus pluvalis* sing 25,000-liter outdoor photobioreactors. 2000. Journal of Applied Phycology 12:499-506).*
City of Cambridge Water Department, Water Operations Division. Water Treatment Information. 2003.*
Olaizola et al. (Commercial production of astaxanthin from *Haemotococcus pluvalis* using 25,000-liter outdoor photobioreactors. 2000. Journal of Applied Phycology 12:499-506).*
Richardson et al. (Effects of Nitrogen Limitation on the Growth and Composition of Unicellular Algae in Continuous Culture. Applied Microbiology (1969) 18(2): 245-250).*
Chaumont, D., "Biotechnology of Algal Biomass Production: A Review of Systems for Outdoor Mass Culutre", Journal of Applied Phycology, vol. 5 No. 6, pp. 593-604,(Jan. 1, 1993) XP 009101993.
Munoz, R. et al.., "Algal-Bacterial Processes for the Treatment of Hazardous Contaminants: A Review", Water Research, vol. 40, No. 15, pp. 2799-2815, (Aug. 1, 2006) XP025039987.
Illman, A. M. et al., "Increase in Chlorella Strains Calorific Values When Grown in Low Nitrogen Medium", Enzyme and Microbial Technology, vol. 27, No. 8 pp. 631-635, (Nov. 1, 2000) XP 002517748.
Pushparaj. B. et al., "Microbial Biomass Recovery Using a Synthetic Cationic Polymer", Bioresource Technology, vol. 43, No. 1, pp. 59-62, (1993) XP002517749.
Blanco, A. M. et al., "Outdoor Cultivation of Lutein-Rich Cells of Muriellopsis sp. in Open Ponds", Applied Microbiology and Biotechnology, vol. 73 No. 6, pp. 1259-1266, (Jan. 2007) XP 002517750.
Chinese Office Action as received in the corresponding Chinese Patent Application No. 200880124455.7 dated Apr. 27, 2013.
Mario R. Tredici, "Mass Production of Microallgae: Photobioreactors", Handbook of Microalgal Culture: Biotechnology and Applied Phycology (2004) pp. 178-214.
Francisco J. L. Gordillo, et al., "Effects of $CO_2$ and nitrogen supply on the biochemical composition of *Ulva rigida* with especial emphasis on lipid class analysis" J. Plant Physiol, 158, 367-372 (2001).

* cited by examiner

*Primary Examiner* — Karen Cochrane Carlson
*Assistant Examiner* — Natalie Moss
(74) *Attorney, Agent, or Firm* — Oblon, McClelland, Maier & Neustadt, L.L.P.

(57) ABSTRACT

The invention relates to a process for the production of algal biomass with a high lipid content, comprising: (a) the production of inocula in order to effect phase (b), in photoreactors; (b) the massive cultivation of the algal biomass in open ponds, inoculated with phase (a); (c) a thickening phase of the algal biomass, effected blandly; (d) an induction phase of the lipid production, wherein modules are used consisting of photoreactors or open ponds; (e) a separation phase of the biomass with a high lipid content.

10 Claims, 9 Drawing Sheets

Bench plant scheme

Biomass concentration in open ponds and photoreactor

Non-polluted algal culture

Algal culture after pollution

P = Protozoa
B = Bacteria
C = Death Algal cell

Scheme of the experiment configuration for the test in continuous

Dry weight in the photoreactor and open pond

→ open pond  → photoreactor  → radiation

Areal productivity of photoreactor, open pond and overall system

→ photoreactor  → open pond  → productivity of the overall system  → radiation

Experimental configuration for the test with maturation pond

Dry weights of the growth pond and maturation pond

—■— pond P-1 —■— maturation P-1M —▲— Radiation

Daily areal productivity of the overall system

—■— overall system productivity —▲— Radiation

PROCESS FOR THE PRODUCTION OF ALGAL BIOMASS WITH A HIGH LIPID CONTENT

CROSS-REFERENCE TO RELATED APPLICATIONS

This application is a National Stage of PCT/EP08/010291 filed Dec. 3, 2008 and claims the benefit of Italian application MI2007A002343 filed Dec. 14, 2007.

The invention relates to a process for the production of algal biomass with a high lipid content.

More specifically, the invention relates to a process for the production of algal biomass with a high lipid content, based on a combination of cultivation systems such as open ponds and photoreactors suitably integrated with thickening systems of the biomass.

Microalgae are currently cultivated for the production of high-value molecules such as poly-unsaturated fatty acids, vitamins and gelling agents which are introduced onto the nutritional, pharmaceutical and cosmetic market.

The best products of algal biomasses use various types of cultivation systems which mainly depend on the algal strain and climatic conditions. Under extremely favourable conditions of temperature and light, such as in Israel and California, for example, open ponds can be successfully used. In Germany, on the contrary, tubular reactors, installed in greenhouses, are used. In Portugal both open ponds and photoreactors are used.

The use of open systems such as open ponds, is also preferred when algal species are cultivated having extremophilic characteristics such as *Dulaniella salina*, capable of growing in environments with salt concentrations of 10-15% and therefore resisting numerous external forms of contamination. This does not occur for species capable of growing in fresh water which, to avoid contamination problems, can be cultivated in closed systems such as photoreactors.

The cultivation of algae for the nutritional, pharmaceutical and cosmetic fields is characterized by rather limited productive capacities with a high value of the products. For this reason, relatively expensive production systems can be tolerated, such as photoreactors, whereas the most widely-used method for the production of microalgae to be used in less valuable commercial fields, such as that of aquaculture, is based on economical cultivation systems, such as open-ponds.

The passage from the above-mentioned fields, in which microalgae are traditionally used, to environmental/energy fields, require the development of technologies which are such as to lead to a strong increase in the productive capacity (in the order of hundreds/thousands of tons per year, to millions of tons per year) and to a strong reduction in the production costs (from hundreds of dollars/kilogram to hundreds of dollars/ton).

The productivity objectives of cultivation systems can be achieved by means of strong improvements aimed at optimizing the adsorption of biologically active radiation and a reduction in photo-inhibition phenomena in order to strongly increment the efficiency of the chlorophyll photosynthesis process.

Numerous research activities are underway, with the aim of optimizing the biomass productivity of the different cultivation systems and of increasing its lipid content.

The production of microalgae with the objective of recycling the $CO_2$ released by industrial plants and producing biomass which can be exploited for energy purposes, such as, for example, vegetable oils to be used for conversion into biodiesel, is at an experimental stage at the moment.

The efforts that are being made for the development of photoreactors do not appear to be resolutive as there are many doubts as to the productivity increases claimed, which, on the other hand, do not appear to be sufficient for obtaining the necessary cost reduction. (Rif.: Patent Application WO 03/094598 "Photobioreactor and Process for Biomass Production and Mitigation of Pollutants in Flue Gases. Company Green Fuel Technology").

Furthermore, there is no evidence in literature relating to the entire process for the production of oils from algal biomasses and their transesterification, except for those described in AICHE Annual Meeting 2006, 12-17 November "Microalgal Oil Extraction and in situ Transesterification" Justin M. Ferrentino and Ihab H. Farag. Chemical Engineering, University of New Hampshire, Kingsbury Hall, 33 College Road, Durham, N.H. 03824, underway at the New Hampshire University, which are attempting to avoid resorting to organic solvents normally used for the extraction of oils, exploiting breakage methods of the cellular walls and subsequent centrifugation or in situ transesterification.

A cultivation system of microalgae has now been found, based on a combination of cultivation systems such as open ponds and photoreactors suitably integrated with thickening systems of the biomass, capable of guaranteeing a high productivity, providing a biomass with a high lipid content, preventing microbiological pollution, maintaining a continuous and stable production with time.

Figure 1:
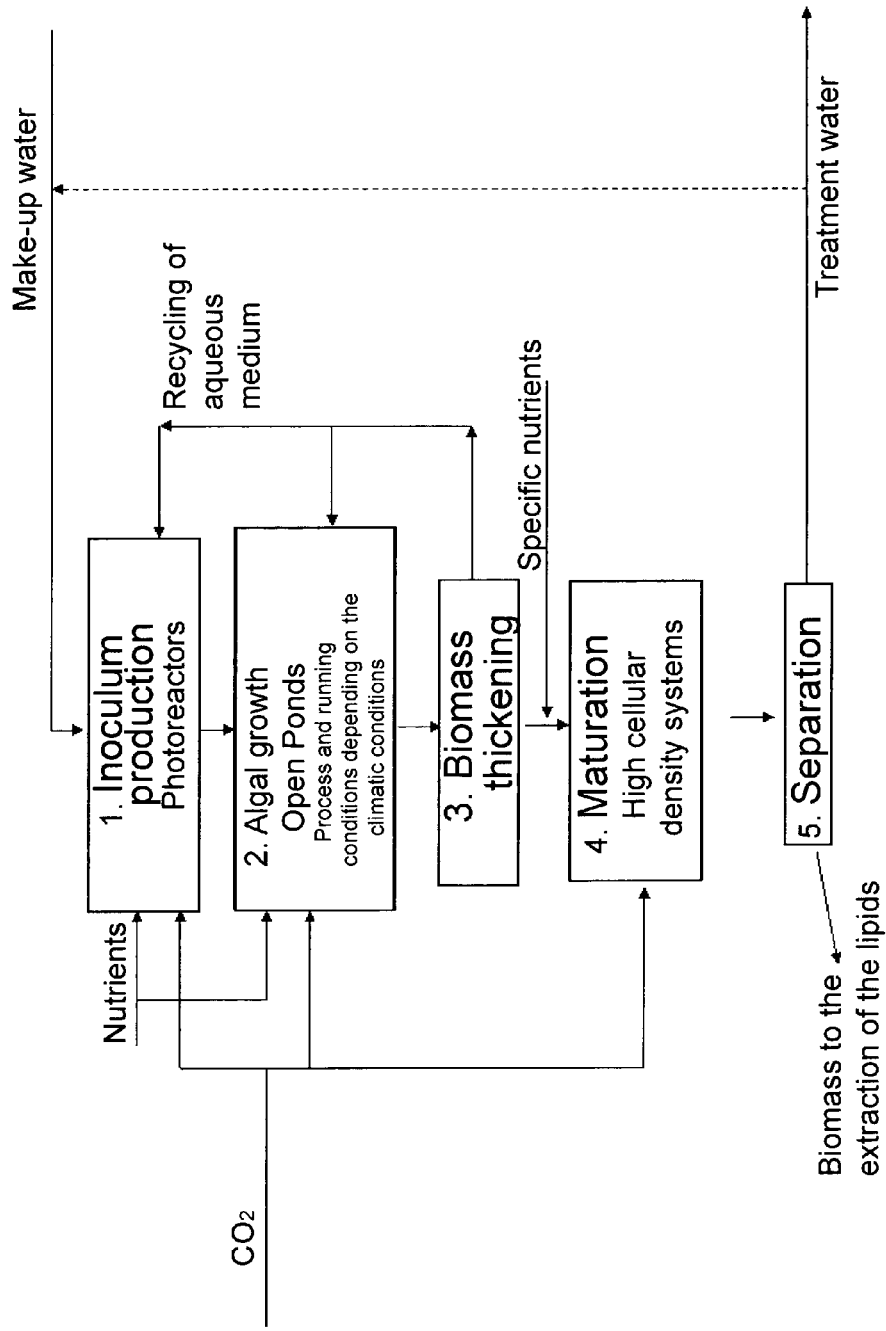
FIG. 1 shows a system for the production of microalgae with a high lipid content.

In particular, an object of the present invention relates to a process for the production of algal biomass with a high lipid content, comprising, in accordance with the scheme shown in FIG. 1:

(a) the production of inocula in order to effect phase (b), in photoreactors;
(b) the massive cultivation of the algal biomass in open ponds, inoculated with phase (a);

(c) a thickening phase of the algal biomass, effected blandly;
(d) an induction phase of the lipid production, wherein modules consisting of photoreactors or open ponds, are used;
(e) a separation phase of the biomass with a high lipid content.

By operating according to the process of the present invention, it is possible to:
i) cultivate species having a high purity degree, suitably managing possible external contamination (emptying of the cultivation ponds and re-inoculation of the same);
ii) cultivate microalgae, limiting the use of photoreactors to the production of inocula of pure species alone, with a consequent cost reduction;
iii) minimize the process volumes necessary for reaching the induction conditions of the lipid production by introducing phase (c);
iv) to make the process continuous by the combined use of various modules of photoreactors and open ponds.

Phase (a) for the production of inocula can be effected in photoreactors having various forms and dimensions: linear tubular reactors having a cylindrical or elliptic shape, parallelepiped or cylindrical planar reactors, such as those described in "Tredici M. R. (2004) Mass production of microalgae: photobioreactors. In Richmond A (ed.) Handbook of Microalgal Culture. Blackwell Publishing, Oxford (UK), pages 178-214". The latter are preferred as they are produced by means of films made of plastic material supported by a simple outer metal structure and they are therefore inexpensive. They are normally run with a hydraulic retention time in the order of 1-2 days and lead to biomass concentrations of about 2 g of dry substance/liter. The ratio between the process volume of the cultivation systems of phase (a) and those of phase (b) depends on the local climatic conditions and on the cultivated algal strain. It is normally within the range of 0.05-0.15 and is preferably equal to 0.1.

The culture broth obtained is used for inoculating cultivation systems on a discontinuous basis (daily or multi-daily).

Alternatively, it can be used on a continuous basis to increase the concentration of the algal biomass in the open ponds of phase (b) and therefore prevent the onset of external contamination phenomena. The aqueous recycling means coming from phase (c), reintegrated with the necessary nutrients (essentially nitrogen and phosphorous salts), is used as growth agent. The aqueous make-up stream can consist of industrial wastewater to be subjected to tertiary treatment. In this case, the algal cultivation metabolizes the substances containing nitrogen and phosphorous contained therein, thus contributing to their purification. As $CO_2$ necessary for algal growth, that contained in industrial flue gases (thermo-electric, hydrogen generation plants, etc.) can be used.

Phase (b) for algal growth can take place in open ponds, both circular and longitudinal. Typical raceway ponds having a longitudinal form are preferred. Also in this case, the hydraulic retention times are 1-2 days. Their running can be either semi-continuous take up a sample of the culture broth and feeding of the growth agents (water and nutrients) in the morning, or in continuous with interruption during the night. This latter option, suitably integrated with control systems of the height of the liquid level of the cultivation system controlled by the algal growth indicators (measurement of the optical density, chlorophyll and possible ratio between them) is preferred.

In the case of the onset of pollution phenomena, the systems used for effecting phase (a) and phase (b) can be periodically decontaminated (water washings or washing with aqueous solutions of disinfectants).

Phase (c) for the thickening of the biomass greatly reduces the process volume (at least ten times) making the use of photoreactors advantageous or drastically reducing the volume of the ponds.

This phase is effected by means of gravitational separation in sedimentation equipment typically used in water treatment plants. It has been found that the sedimentation of algal strains of fresh water, such as, for example, *Scenedesmus* sp. is greatly facilitated by the use of cationic polyelectrolytes (i.e. polyacryloamides) used in a quantity of 2-5 ppm (passage of the algal concentration from 0.4-0.5 g/liter to 40-50 g/liter in about 1.5 hours).

Phase (d) for the cell maturation is effected with the objective of obtaining cultivation conditions which lead to an increase in the content of the lipid fraction of the biomass. In this respect, the growth medium will be maintained with limited nitrogen, consequently the stream coming from phase (c) will be mainly integrated, if necessary, with phosphorous sources and possibly micronutrients. The cultivation systems which can be used in this phase can consist of open ponds and photoreactors. The biomass concentration in the stream coming from phase (c) is established depending on the maturation system selected (in the order of g/liter for open ponds and tens of g/liter for photoreactors).

Phase (e) can be effected with systems analogous to those adopted in phase (c). The aqueous phase which is separated can be directly sent to the final treatment before being discharged or recycled, after purging, to avoid the accumulation of metabolites in the whole system.

The first option is adopted when the algal cultivation is used not only for the production of biomass but also for the purification of wastewater (tertiary treatment). The second option, on the contrary, is used when wastewater is not available and it is necessary to limit the demands for water. The purging stream generally ranges from 1 to 20%, preferably equal to 10% of the total aqueous stream generated by the separation.

EXAMPLE 1

Semi-Continuous Cultivation with Daily Dilution

Mono-Algal Species *Chlorella sorokiniana*.

The collection strain *Chlorella sorokiniana* was used, which normally grows in fresh water.

The inoculum to be introduced into the culture systems described hereunder, was prepared as follows:
  a sample of mono-algal culture previously preserved at −85° C. in a 10% solution of glycerine, was defrosted by leaving it at room temperature, it was then centrifuged to remove the supernatant.
  the cellular paste thus obtained was inoculated into three 250 ml flasks containing 50 ml of solution containing nutrients.
  The culture was left to grow in an illuminated climatic chamber, at a constant temperature of 30° C. in the presence of $CO_2$ at 0.5% in air.
  After about one week, the flask reached a concentration of 0.2 g/l, and this culture was used as inoculum for three 1 liter flasks containing 500 ml of solution containing nutrients and placed in a climatic chamber.
  After two days, the culture had a concentration of 0.4 g/l, and formed the inoculum of the 5 liter Roux bottles used in the laboratory experimentation for the preparation of the inoculum necessary for the subsequent experimentation.

A total of 60 liters of inoculum were prepared, using 12 Roux bottles (for the subsequent tests, the inoculum was proportionally reduced to the volume of the reactors) which were illuminated by means of 17,500 Lux tungsten lamps. The $CO_2$ necessary for the growth was supplied from cylinders and fed at an average flow of 25 liters/hour per Roux bottle. The pH of the single Roux bottles was measured, from time to time, and when shifts of ±0.2 units with respect to neutrality were observed, the flow of $CO_2$ was manually modified.

Cultivation Medium:

all the cultivation systems (flasks, roux bottles, photoreactors, open ponds) were tested using the following growth medium:

| | |
|---|---|
| $KNO_3$ | 1.75 g/l |
| $KH_2PO_4$ | 1.25 g/l |
| $K_2HPO_4$ | 0.1 g/l |
| $CaCl_2$ | 0.01 g/l |
| $FeSO_4 \cdot 7H_2O$ | 0.003 g/l |
| $MgSO_4 \cdot 7H_2O$ | 1.5 g/l |

Micro-elements: 1 ml/l of the following solution: $H_3BO_3$ 2.86 g, $MnCl_2 \cdot 4H_2O$ 1.81 g, $CuSO_4 \cdot 5H_2O$ 80 mg, $ZnSO_4 \cdot 7H_2O$ 220 mg, $Na_2MoO_4$ 210 mg, $FeSO_4 \cdot 7H_2O$ 25 g, EDTA 33.5 g and 1 drop of concentrated $H_2SO_4$ per liter. Operating pH: 7.0.

The above composition was obtained by modifying the typical cultivation medium M4N indicated in literature, for the cultivation of microalgae. In particular, the $KNO_3$ content was reduced (from 5.0 to 1.75 g/l, in the classical composition a strong excess of the nitrogenated compound is envisaged, thus avoiding daily addition), $K_2HPO_4$ added in a quantity of 0.1 g/l, and the content of $MgSO_4 \cdot 7H_2O$ reduced (from 2.5 to 1.5 g/l).

Experimental System

The micro-alga *Chlorella sorokiniana* was tested using a bench-type system consisting of open ponds and a photoreactor installed outdoor.

The plant included four cultivation units: three 375 liter open ponds having an illuminated surface of 2.5 $m^2$ and a photoreactor of 39 liters having a illuminated surface of 0.98 $m^2$. The open ponds, following the design of those forming the systems on a large scale (paddle wheel-mixed raceway ponds), were equipped with a paddle wheel to keep the microalgal culture under constant agitation (rate of 30 cm/s) and had a longitudinal division so as to create, by means of the movement of the paddle, a continuous and circular flow.

The photoreactor consisted of a set of 10 tubes each with a diameter of 45 mm and 2 m long. The stirring of the culture, in this case was guaranteed by gas ($CO_2$ and air, alternatively) which was sent inside the tubes which, in addition, were equipped with a cooling system to prevent the temperature from being higher than 32° C. The open ponds were not equipped with a temperature control system. Each unit was equipped with sensors for monitoring the temperature, pH and concentration of the dissolved oxygen.

The carbon source consisted of gaseous $CO_2$, directly sent inside the reactor and regulated by means of pH measurement.

Figure 2:
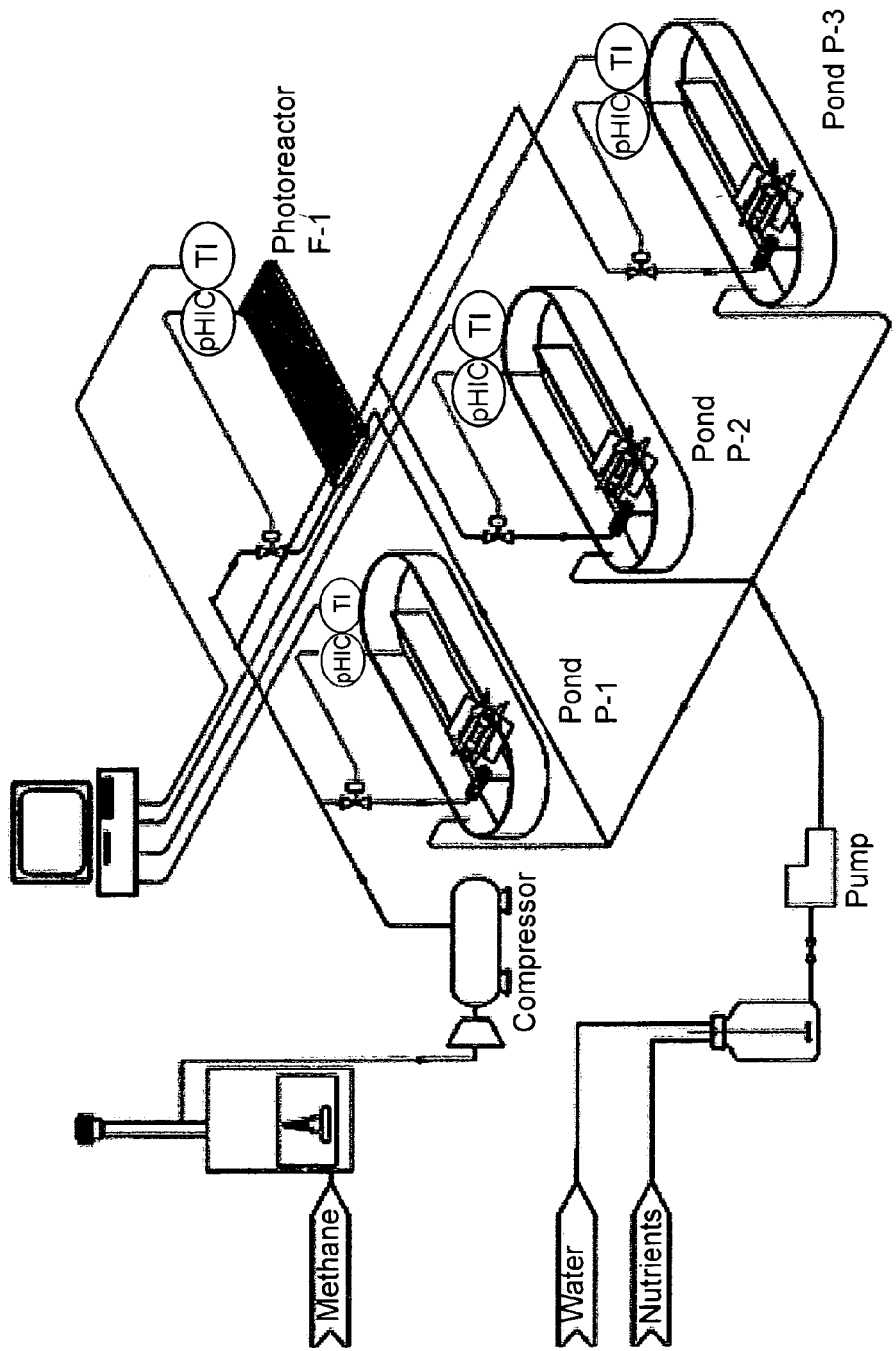
FIG. 2 shows a scheme of the bench plant, in the scheme it is indicated that the source of $CO_2$ used consisted of exhausted gases coming from a boiler fed with methane of the supply system.

FIG. 2 shows a scheme of the bench plant described above, in the scheme it is indicated that the source of $CO_2$ used consisted of exhausted gases coming from a boiler fed with methane of the supply system.

The experimentation carried out with the experimental configuration described above, is illustrated hereunder.

The photoreactor F-1 and the three open ponds P-1, P-2, P-3 were inoculated in an amount of 5% of their volume, with the algal cultivations effected in laboratory roux bottles, as previously specified. The photoreactor was inoculated three days after the ponds. After about a week of cultivation, the plateau conditions were reached, with biomass concentrations of 0.3-0.5 g/l in the ponds and 1-2 g/l in the photoreactor. The systems were then run in discontinuous, at the following dilution rates: pond P-1 30%, pond P-2 45%, pond P-3 60% and photoreactor F-1 30%. The take up samples of the culture broth and the feeding in the growth medium in the quantities necessary for effecting the required dilutions, were effected in the early morning (from 7 to 8).

During the test, the dry weight of the culture was monitored daily, together with the solar radiation, temperature, concentration of dissolved oxygen and pH.

Figure 3:
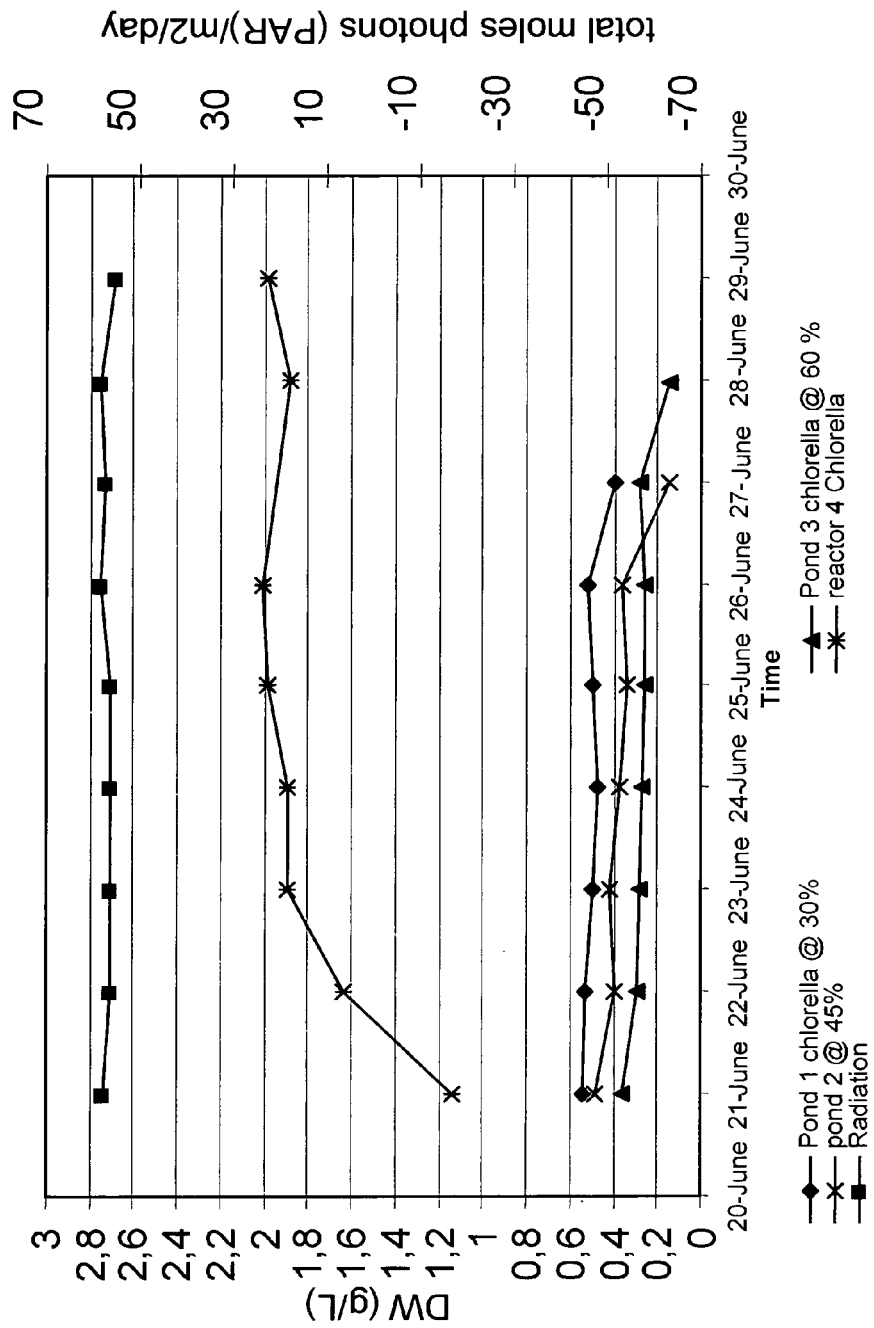
FIG. 3 shows the trends of the concentration of the algal biomass in the open ponds and photoreactors.

FIG. 3 shows the trends of the concentration of the algal biomass in the open ponds and photoreactors. It can be observed, as is well-known in literature, that the concentration values of cultures in closed systems (photoreactor) are higher with respect to the those of open systems.

Figure 4:
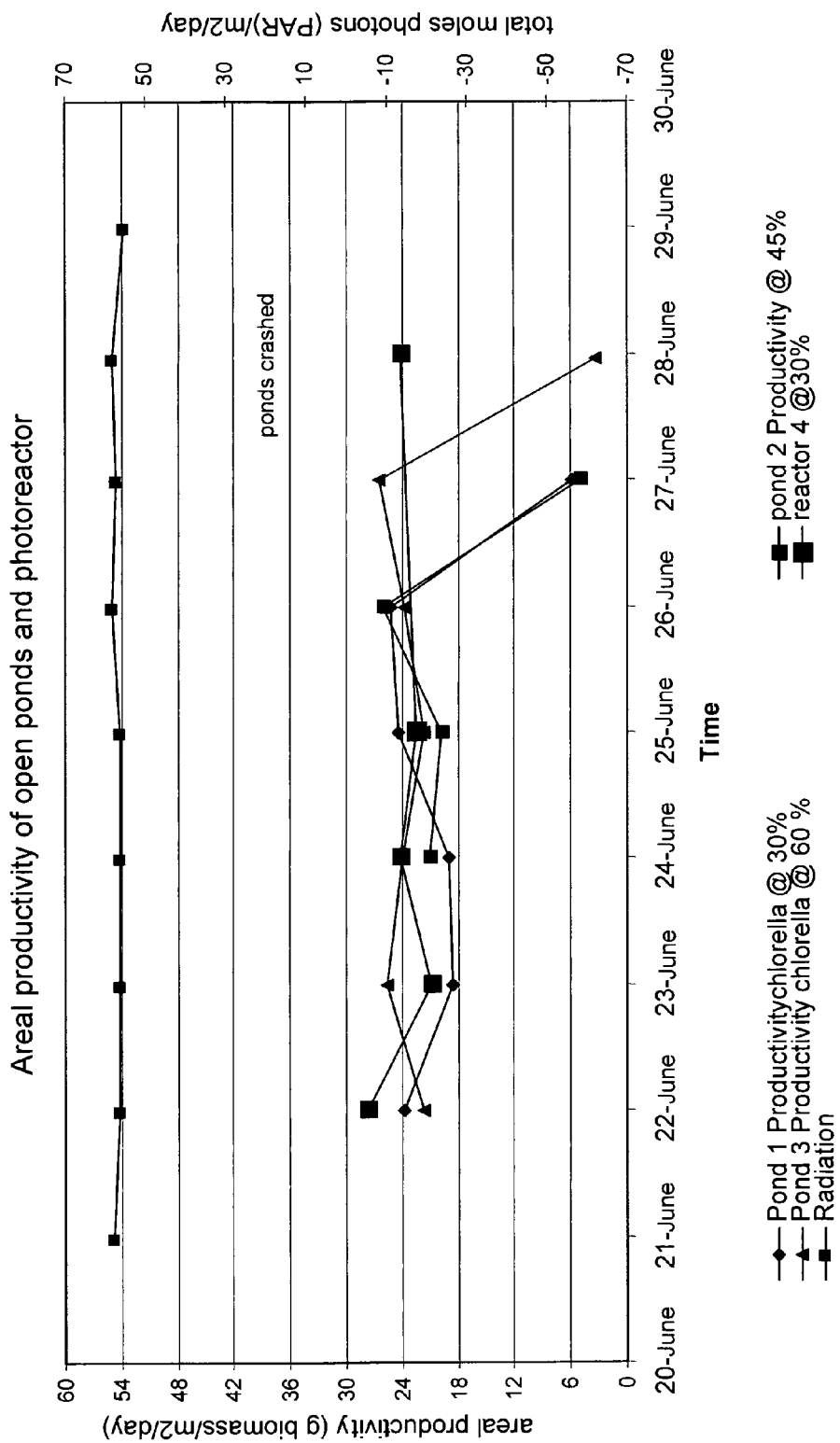
FIG. 4 shows the respective areal productivity values of the different growth systems.

FIG. 4 shows the respective areal productivity values of the different growth systems, calculated by means of the relation:

$$(C \times V)/S/T$$

wherein:

C=biomass concentration g/l
V=volume of the culture taken up daily (liters)
S=surface of the cultivation systems (foot print, $m^2$)
T=time (1 day)

Samples of algal biomass at the first, third and sixth day of experimentation in semi-continuous, taken up from the open ponds and photoreactor were analyzed to determine the content of lipids, proteins, carbohydrates, carotenoids and chlorophyll. The methods used and the results obtained are shown in table 1.

It can be observed that the content of the substances analyzed proved to be relatively stable, particularly as far as the lipid content is concerned.

As can be noted in the previous figures, the open ponds proved to have a poor stability over a period of time, with this experimental configuration. After about ten days of experimentation, in fact, the algal cells suffered sudden pollution on the part of bacteria and protozoans, with the consequent almost total disappearance of the algal proliferation, in about two days. The photoreactor, on the contrary, showed a constant productivity with time.

Figure 5:
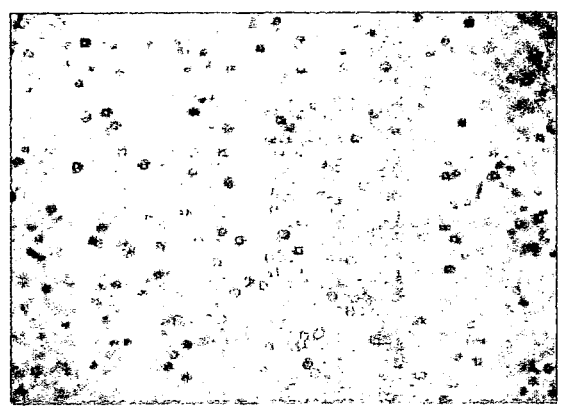
FIG. 5 shows microscope photographs of the cultures, before pollution.
Figure 6:
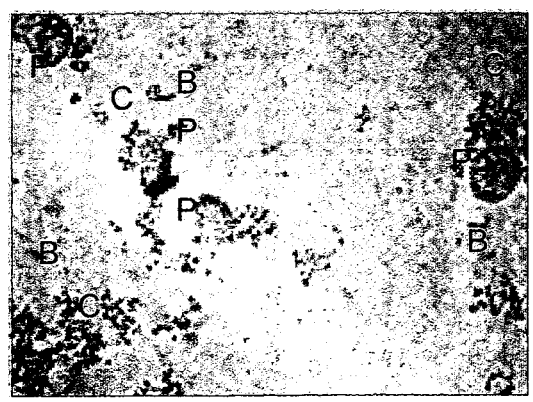
FIG. 6 shows microscope photographs of the cultures, after pollution.

FIGS. 5 and 6 show microscope photographs of the cultures, before and after pollution. In FIG. 6 the presence of several protozoans which proliferate in the culture medium can be observed. This can be mainly attributed to the type of cultivation system which, due to its wide exposure to the outside environment, makes it easily exposable to colonization on the part of other living species which grow in competition with that which is being cultivated. It should be noted that these phenomena can be favoured by the relatively low concentration of the algal species which tends to yield with time.

EXAMPLE 2

Cultivation in Continuous with Night Interruption

In order to attempt to solve problems of pollution of the ponds observed during the previous test, a cultivation method was adopted, based on continuous inoculation of the ponds with the biomass in monoculture coming from the photoreactor and constant dilution of the ponds themselves. This was to favour the proliferation of the algal biomass and to reduce that of the polluting species.

Figure 7:
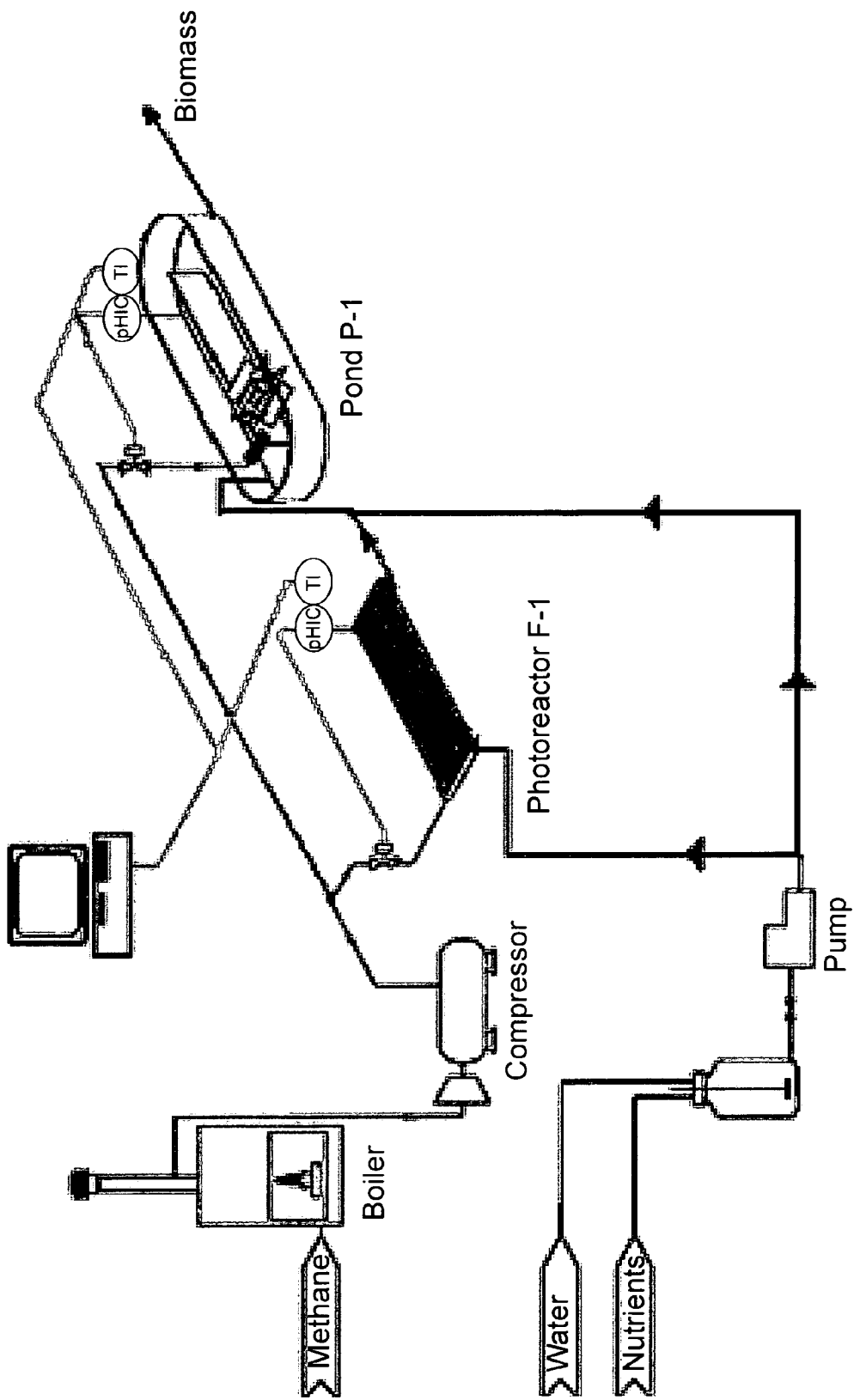
FIG. 7 shows a process scheme of the experiment configuration for the test discussed in Example 2.

The process scheme is shown in FIG. 7.

A dilution was used equal to 30% which, on the basis of the previous tests, gave the highest concentrations of the biomass and the productivity remained substantially analogous to that observed with the highest dilutions.

The photoreactor F-1 alone and the pond P-1, connected in series, were tested.

The procedure for the production of the inocula for the two growth units was that described in example 1.

The photoreactor was fed with the culture medium, in continuous, for 12 hours a day, at a flow-rate of 1.0 liter/hour. The stream leaving the photoreactor was fed to the pond P-1. The latter was also fed with the culture medium at a flow-rate of 8.4 liter/hour. The flow-rate at the outlet of this system therefore proved to be equal to 9.4 liter/hour. In this way, a dilution rate is maintained equal to that used in test 1, with a dilution of about 30% (9.4 l/hr*12 hours/day: 375 l=0.30).

Analogously, the dilution rate of the photoreactor proved to be equal to 30% (1.0 l/hr*12 hours/day: 40 l=0.30).

Bearing in mind that the pond was fed for 12 hours a day, the overall hydraulic retention time proved to be equal to 3.3 days (375 l: 112.8 l/day=3.3 days) analogously to that of the photoreactor (40 l: 12 l/day=3.3 days).

The system proved to be stable under these conditions and the pollution phenomena found during the previous test, were not observed. The experiment was considered concluded after about 30 days.

Figure 8:
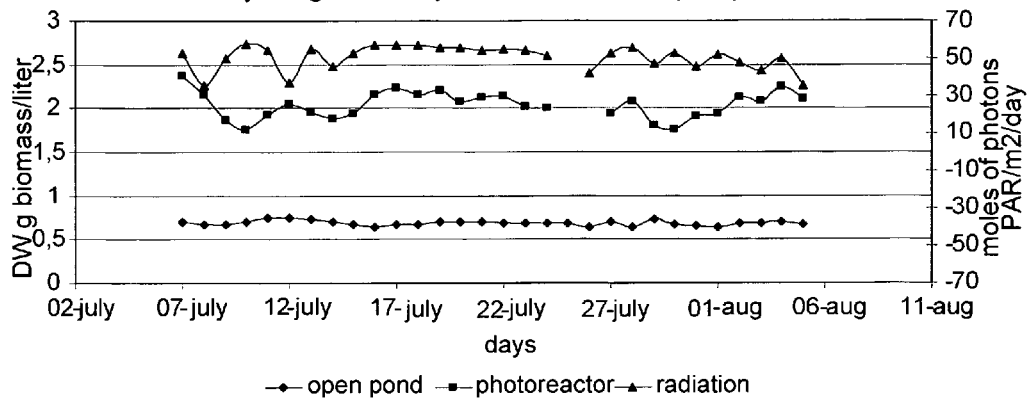
FIG. 8 shows the trend of the biomass concentration and areal productivity found in the photoreactor and open pond.
Figure 9:
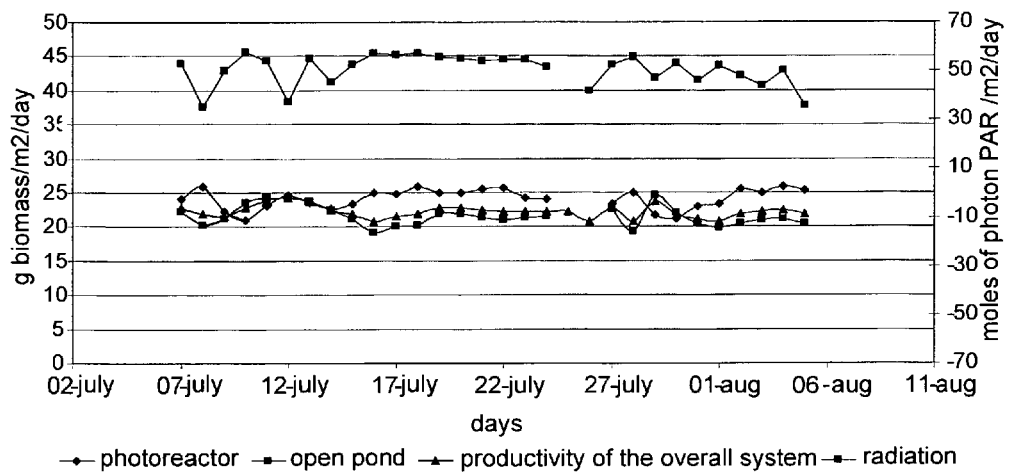
FIG. 9 shows the trends of the biomass concentration and areal productivity found in the open pond and overall system.

FIGS. 8 and 9 show the trends of the biomass concentration and areal productivity found in the two cultivation systems.

A comparison of FIG. 3 with FIG. 8 shows that the biomass concentration in the photoreactor proved to be in line with those observed in example 1 (about 2 g/l) whereas that of the pond proved to be higher (about 0.7 against 0.5 g/l). The increase in concentration in the pond is probably due to the contribution of the algal biomass fed in continuous to the photoreactor (about 2 g/hour). The mass flow-rate, under regime conditions, leaving the open pond was therefore equal to 6.6 g of biomass/hour approximately.

Also in this case, samples of algal biomass were taken every three days during the experimentation in continuous from both the open ponds and photoreactor. The analysis values of the lipids, proteins, carbohydrates, carotenoids and chlorophyll are indicated in Table 2.

It can be observed that the cellular composition is very similar to that specified in the test of Example 1.

EXAMPLE 3

Cultivation in Continuous with Final Maturation Open Pond

In order to increase the lipid content, the biomass was subjected to stress by nitrogen deficiency. For this purpose, a new experimental configuration was produced by adding, downstream of the system described in the previous test, a further pond (P-1M), indicated as maturation pond. It had a useful volume of 112.8 liters (dimensions: 0.75 square meters base, by 15.0 cm of culture height) also managed in continuous. The streams entering and leaving the maturation pond were equal to 9.4 l/hour. Its useful volume was selected so as to obtain a hydraulic retention time equal to 1 day (with respect to 3.3 days of the other two reactors).

The condition of stress by nitrogen limitation was effected by eliminating the feeding of the culture medium and $CO_2$.

Figure 10:
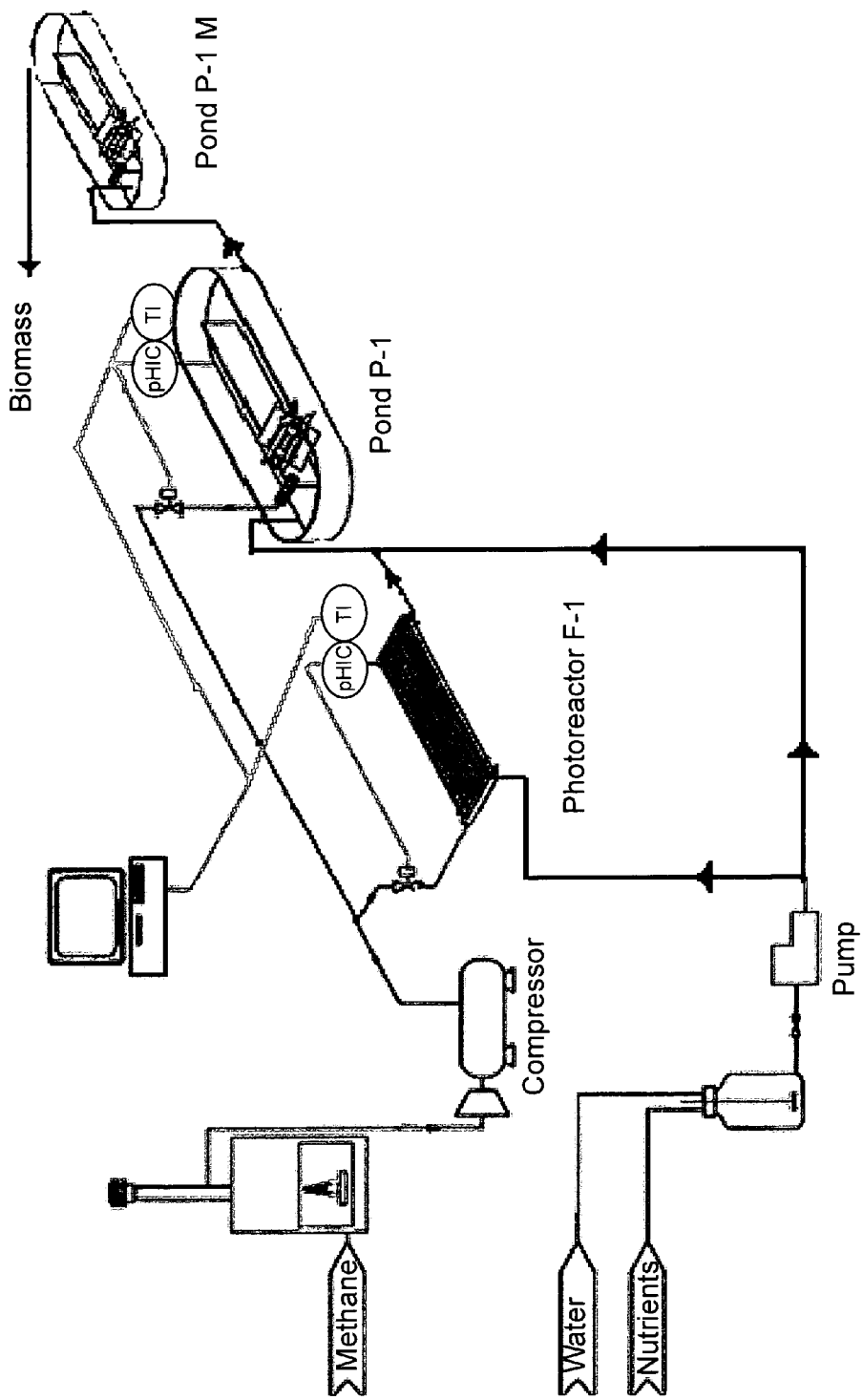
FIG. 10 shows the experimental configuration for the test with a maturation pond.

The plant scheme for this test is shown in FIG. 10.

In order to prevent the maturation pond from being fed with nitrogen coming from an excess of $KNO_3$ fed to the pond P-1 (a condition which is normally adopted in traditional growth systems), in spite of the non-administration of the culture medium, the concentration of $KNO_3$ was reduced in the culture medium (from 1.75 g/l to 0.45 g/l) entering the above pond so as to supply a quantity which was strictly necessary for the micro-algal growth.

The concentration of nitrogen in the stream leaving this pond, which was fed to the maturation pond, was consequently extremely low with values oscillating around 0.006 g/liter.

It should be noted that to reach this result, it was not necessary to vary the concentration of $KNO_3$ in the culture medium being fed to the photoreactor F-1 (again 1.75 g/l), consequently leaving its growth conditions unaltered.

Figure 11:
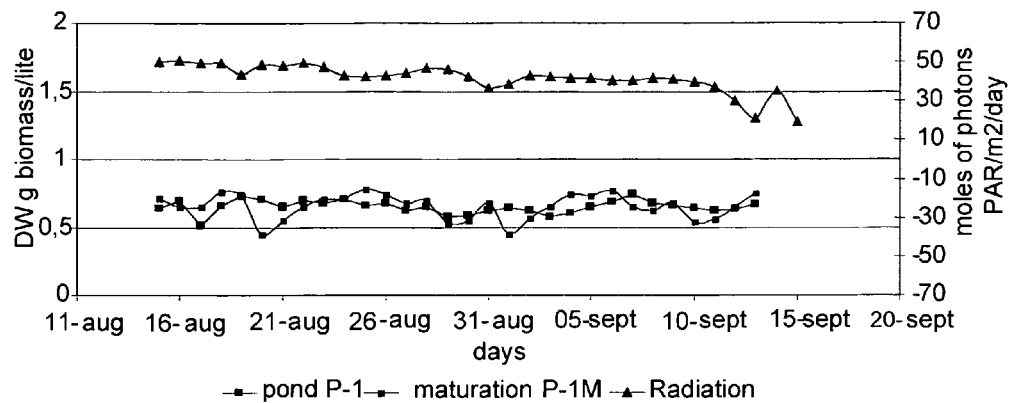
FIG. 11 shows the dry weight values of the ponds P-1 and P-1M.
Figure 12:
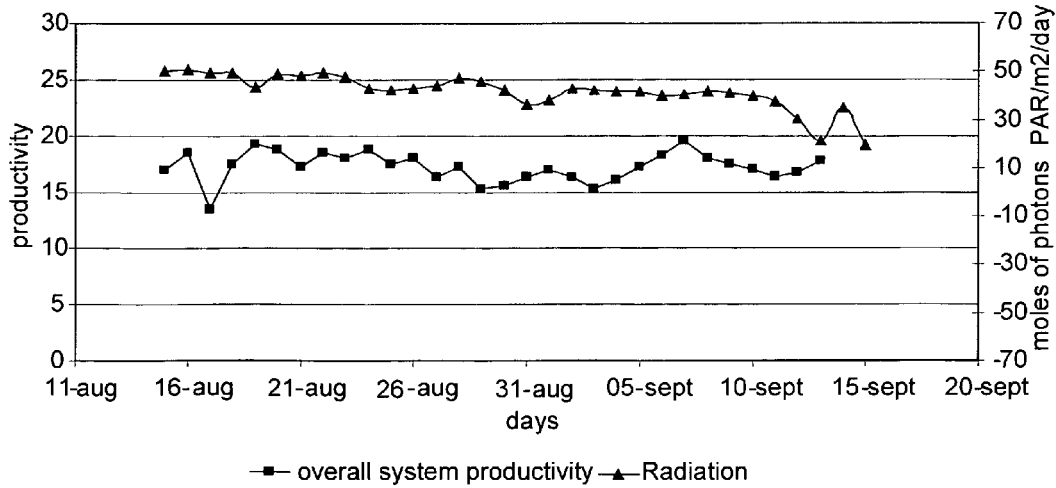
FIG. 12 indicates the daily areal productivity of the algal biomass of the whole system consisting of photoreactor, growth pond P-1 and maturation pond P-1 M.

Under these experimental conditions, the productivity of the maturation pond was almost null but the dry weight values remained very similar to those of the pond P-1, FIG. 11 shows the dry weight values of the ponds P-1 and P-1M, whereas FIG. 12 indicates the daily areal productivity of the algal biomass of the whole system consisting of photoreactor, growth pond P-1 and maturation pond P-1 M.

On observing the values of the cellular composition, it is evident that during the maturation phase, the cells react to the stress condition by producing more lipids to the detriment mainly of the proteins (table 3).

For the purpose of lipid productivity per surface unit, the increase in percentage of lipids in the cells widely compensates the lower areal productivity of the biomass of the whole system as shown in the following calculation, confirming the efficacy of the solution adopted.

EXAMPLE 2

Lipids Produced $$22.56 \text{ g biomass/m}^2/\text{day(Overall areal productivity)} \times 0.16(\% \text{ lipids in the biomass})=3.6 \text{ g of lipids/m}^2/ \text{day(daily areal productivity of lipids)}.$$

EXAMPLE 3

Lipids Produced $$17 \text{ g biomass/m}^2/\text{day(Overall areal productivity)} \times 0.37(\% \text{ lipids in the biomass})=6.29 \text{ g of lipids/} \text{m}^2/\text{day(daily areal productivity of lipids)}.$$

As it can be observed, an increase in the production of lipids of over 40% was registered.

TABLE 1

Analysis of the algal biomass produced during the test of example 1.

| Substance | Analytical method | Quantity (% w/w dry) |
| --- | --- | --- |
| Proteins | Bradford, Bio-rad Protein Assay. Analyt. Biochem 72, 248 (1976) | 61.7 ± 2.5 |
| Chlorophyll a + b | SCOR-UNESCO method (1996) | 3.64 ± 0.2 |
| Carotenoids | Kubin & Kubinova (1985) | 0.93 ± 0.1 |
| Lipids | Bligh and Dyer, Journal of Biochem Physiology 37, 911-917 (1959) | 14.33 ± 1.3 |
| Carbohydrates | Trevelyan and Harrison, Arch. Biochem. Biophys. 39(2): 419-39 (1952) | 17.94 ± 0.5 |

TABLE 2

Analysis of the algal biomass produced during the test of example 2.

| Substance | Analytical method | Quantity (% w/w dry) |
|---|---|---|
| Proteins | Bradford, Bio-rad Protein Assay. Analyt. Biochem 72, 248 (1976) | 60.3 ± 2.0 |
| Chlorophyll a + b | SCOR-UNESCO method (1996) | 3.23 ± 0.3 |
| Carotenoids | Kubin & Kubinova (1985) | 0.87 ± 0.2 |
| Lipids | Bligh and Dyer, Journal of Biochem Physiology 37, 911-917 (1959) | 16.10 ± 1.1 |
| Carbohydrates | Trevelyan and Harrison, Arch. Biochem. Biophys. 39(2): 419-39 (1952) | 16.74 ± 0.5 |

TABLE 3

Analysis of the algal biomass produced during the test of example 3.

| Substance | Analytical method | Quantity (% w/w dry) |
|---|---|---|
| Proteins | Bradford, Bio-rad Protein Assay. Analyt. Biochem 72, 248 (1976) | 43.2 ± 2.3 |
| Chlorophyll a + b | SCOR-UNESCO method (1996) | 0.9 ± 0.2 |
| Carotenoids | Kubin & Kubinova (1985) | 1.1 ± 0.3 |
| Lipids | Bligh and Dyer, Journal of Biochem Physiology 37, 911-917 (1959) | 37.2 ± 1.5 |
| Carbohydrates | Trevelyan and Harrison, Arch. Biochem. Biophys. 39(2): 419-39 (1952) | 15.2 ± 0.5 |

The invention claimed is:

1. A process for producing an algal biomass with a high lipid content, the process comprising in sequence:
   (a) producing an algal inocula to effect phase (b), in photoreactors;
   (b) massive cultivating of the algal biomass in open ponds, inoculated with phase (a);
   (c) gravitationally separating the algal biomass to thicken the algal biomass;
   (d) cultivating the thickened algal biomass in modules of photoreactors or open ponds different from the open ponds in (b) in a growth medium maintained under nitrogen limitation to induce lipid production in the algal biomass, wherein said nitrogen limitation comprises eliminating feeding the growth medium and providing $CO_2$;
   (e) separating the algal biomass with a high lipid content.

2. The process according to claim 1, wherein phase (a) for the preparation of the inocula is carried out in photoreactors having a cylindrical shape composed of a film of plastic material, supported by a simple external metal structure, the photoreactors positioned in the same plane relative to each other.

3. The process according to claim 1, wherein the inocula prepared during phase (a) are used for inoculating open ponds on a discontinuous basis or continuous basis.

4. The process according to claim 1, wherein the gravitationally separation yields aqueous medium and the process further comprises recycling the aqueous medium, supplemented with nutrients as a growth agent of phase (a) and phase (b), wherein the nutrients comprise nitrogen and a phosphorous salt.

5. The process according to claim 4, further comprising adding to the recycled aqueous medium coming from phase (c) an aqueous stream of industrial wastewater to be subjected to tertiary treatment.

6. The process according to claim 1, the carbon dioxide provided is from industrial flue gases.

7. The process according to claim 1, wherein the cultivation of the algal biomass occurs in open ponds having a longitudinal shape, of the paddle wheel-mixed raceway ponds type, equipped with a paddle wheel to keep the microalgal culture under constant agitation.

8. The process according to claim 1, wherein the open ponds are run semi-continuously, with taking a sample of the culture and adding growth agents in the morning, or continuously during the day with interruption during the night.

9. The process according to claim 1, wherein the gravitational separation comprises gravitational separation in sedimentation basins used in water treatment plants.

10. The process according to claim 9, wherein the thickening of the biomass further comprises adding cationic polyelectrolytes.

* * * * *